United States Patent
Seaman

(10) Patent No.: US 12,194,178 B1
(45) Date of Patent: Jan. 14, 2025

(54) BEVERAGE CONTAINER SANITIZING DEVICE

(71) Applicant: Jeffrey J. Seaman, San Antonio, TX (US)

(72) Inventor: Jeffrey J. Seaman, San Antonio, TX (US)

( * ) Notice: Subject to any disclaimer, the term of this patent is extended or adjusted under 35 U.S.C. 154(b) by 226 days.

(21) Appl. No.: 17/524,203

(22) Filed: Nov. 11, 2021

(51) Int. Cl.
*A61L 2/18* (2006.01)
*A46B 9/02* (2006.01)
*A46B 11/00* (2006.01)

(52) U.S. Cl.
CPC ............... *A61L 2/18* (2013.01); *A46B 9/028* (2013.01); *A46B 11/001* (2013.01); *A46B 2200/3006* (2013.01); *A61L 2202/15* (2013.01); *A61L 2202/16* (2013.01); *A61L 2202/17* (2013.01); *A61L 2202/23* (2013.01)

(58) Field of Classification Search
CPC ......................................................... A61L 2/18
See application file for complete search history.

(56) References Cited

U.S. PATENT DOCUMENTS

| | | | |
|---|---|---|---|
| 4,651,890 A | 3/1987 | Coker et al. | |
| 6,090,215 A | 7/2000 | Cooper | |
| 6,105,200 A | 8/2000 | Cooper | |
| 6,254,692 B1 | 7/2001 | Cooper | |
| 6,427,861 B1 | 8/2002 | Cho | |
| 9,162,798 B2 | 10/2015 | Hands | |
| 10,709,302 B2 | 7/2020 | Roy et al. | |
| 2008/0038167 A1* | 2/2008 | Lynn | A61M 39/165 422/294 |
| 2011/0314619 A1* | 12/2011 | Schweikert | A61C 19/002 15/160 |
| 2012/0039765 A1* | 2/2012 | Solomon | A61L 2/16 422/292 |

OTHER PUBLICATIONS

Cleaning Gunk from an Aluminum Can Top. Product Listing [online]. robot room [retrieved on Mar. 5, 2021]. Retrieved from the Internet: <URL: http://www.robotroom.com/PopTopCleaner.html>.
Ever Wipe Off Your Soda Can Top? With Over 250 Billion Cans Consumed Per Year, Everyone Has!. Product Listing [online]. ©Copyright 1997-2015 [retrieved on Mar. 5, 2021]. Retrieved from the Internet: <URL: https://www.prweb.com/releases/2011/5/prweb8412815.htm>.

* cited by examiner

*Primary Examiner* — Donald R Spamer
(74) *Attorney, Agent, or Firm* — Cramer Patent & Design, PLLC.; Aaron R. Cramer

(57) ABSTRACT

A beverage container sanitizing device is a cleaning device having a flat tubular structure with an interior helical scrubbing brush and a means of dispensing a sanitizing liquid. The interior of the device is provided with a reservoir that holds food safe (non-toxic) sanitizing solution. The solution is automatically applied to the exterior of a beverage can or bottle, via an internal brush, whereupon a slight twisting motion cleans the exterior surface of the beverage container.

1 Claim, 6 Drawing Sheets

BEVERAGE CONTAINER SANITIZING DEVICE

RELATED APPLICATIONS

Non-applicable.

FIELD OF THE INVENTION

The present invention relates to a sanitizing device for a beverage container.

BACKGROUND OF THE INVENTION

Everyone probably has had the unfortunate circumstance of dealing with a dirty and soiled beverage can or bottle. While at home, it is a simple manner to simply wash the offending container under running water prior to opening. However, when away from home, such cleaning is typically much more difficult or even impossible. Many are forced to simply wipe the offending container, perhaps with a shirt or jacket, and hope for the best. This action obviously exposes the user to invisible dirt, germs, bacteria, and viruses.

In the times of a pandemic such as COVID-19, such contaminants can easily make one ill or even cause their death in severe cases. Accordingly, there exists a need for a means by which both visible and invisible contaminants on beverage cans and bottles can be easily and completely removed without the necessity of running water. The development of the beverage container sanitizing device fulfills this need.

SUMMARY OF THE INVENTION

The inventor has recognized the aforementioned inherent problems and lack in the art and observed that there is a need for a beverage container sanitizing device that has a first outer housing adapted to be disposed on top of a beverage can, a first end having a can bristle insert with a plurality of vertical bristles and a plurality of horizontal bristles that are adapted to contact a can top, a can rim, and a plurality of can sides, a second end having a can wiping pad insert held within the first outer housing, a sanitizer reservoir disposed on an upper portion of the first outer housing to hold a food safe sanitizing liquid, and a collapsible section disposed on the first outer housing for compact storage of the beverage container sanitizing device when not in use.

The first outer housing may be adapted to be turned back and forth along a first rotating travel path in relation to the beverage can during cleaning. A top of the first outer housing may include a plurality of anti-slip protrusions to facilitate a turning process. The first outer housing that may sit atop the beverage can may be 1-½ inches tall. The first outer housing that may sit atop the beverage can may be 3 inches tall. The beverage container sanitizing device may further comprise a non-toxic food-safe liquid sanitizer added to the vertical bristles and the horizontal bristles to facilitate cleaning. The beverage container sanitizing device wherein several drops of the non-toxic food-safe liquid sanitizer may be added to the vertical bristles and the horizontal bristles. The can wiping pad insert may be held within the first outer housing with a first threaded connection. The first threaded connection may allow for removal of the can bristle insert for cleaning and replacement of the first outer housing. The first threaded connection may be between the first outer housing and the can wiping pad insert.

The first threaded connection may allow for removal of the can wiping pad insert for cleaning, replacement, or usage of the first outer housing with the can bristle insert. The can wiping pad insert may be disposed on the second end. The can wiping pad insert may include an absorbent pad that contacts the can top, the can rim, and the can sides that removes a plurality of remnants of the food-safe liquid sanitizer. The food safe sanitizing liquid may be a purely foodservice surface sanitizer. The beverage container sanitizing device may further comprise a second outer housing that may sit atop the beverage bottle. The second outer housing may include a collapsible section that may allow the second outer housing to be reduced in size to save on space storage requirements when not being used. The second outer housing may be turned back and forth along a second rotating travel path in relation to the beverage bottle during cleaning. The second outer housing may be 2 inches tall. The second outer housing may be 3 inches tall. The beverage container sanitizing device may further comprise a protective cover disposed on the bottom of the outer housing to protect an interior of the beverage container sanitizing device from contamination when not in use.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
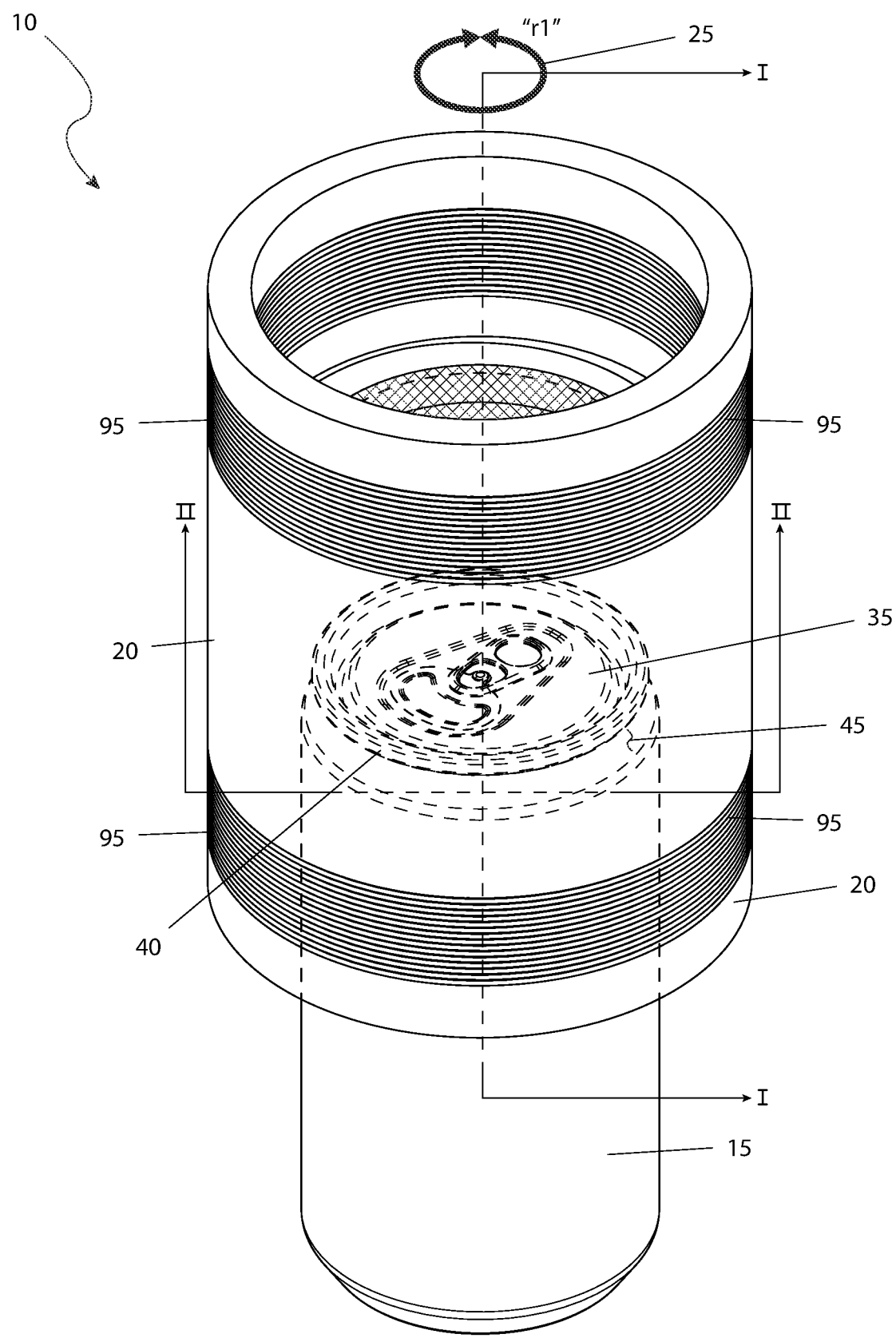
FIG. 1 is a perspective view of the beverage container sanitizing device 10, according to the preferred embodiment of the present invention.

DESCRIPTIVE KEY 10 beverage container sanitizing device
15 beverage can
20 first outer housing 25 first rotating travel path "r1"
30 anti-slip protrusions
35 can top
40 can rim
45 can side
50 can bristle insert
55 vertical bristles
60 horizontal bristles
65 food-safe liquid sanitizer
70 first threaded connection
71 sanitizer reservoir
72 protective cover
75 can wiping pad insert
80 absorbent pad
85 beverage bottle
90 second outer housing
95 collapsible section
100 second rotating travel path "r2"
105 bottle top
110 bottle cap
115 bottle sides
120 bottle bristle insert
125 second threaded connection
130 bottle wiping pad insert

DESCRIPTION OF THE PREFERRED EMBODIMENTS

The best mode for carrying out the invention is presented in terms of its preferred embodiment, herein depicted within FIGS. 1 through 8. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a perspective view of the beverage container sanitizing device 10, according to the preferred embodiment of the present invention is disclosed. The beverage container sanitizing device (herein also described as the "device") 10, is portable and designed to clean and sanitize beverage cans 15 and beverage bottles 85. The preferred embodiment is designed to clean the top of a beverage can 15. It includes a first outer housing 20 that sits atop the beverage can 15 it is approximately three inches (3 in.) tall and one and one-half inches (1-½ in.) tall. It is turned back and forth along a first rotating travel path "r1" 25, in relation to the beverage can 15 during the cleaning process. The top of the first outer housing 20 is provided with anti-slip protrusions 30 to facilitate the turning process. The cleaning process, to be further described herein below, provides for the cleaning of the can top 35, the can rim 40, and the upper portion of the can sides 45 and is performed before the beverage can 15 is opened.

Figure 2:
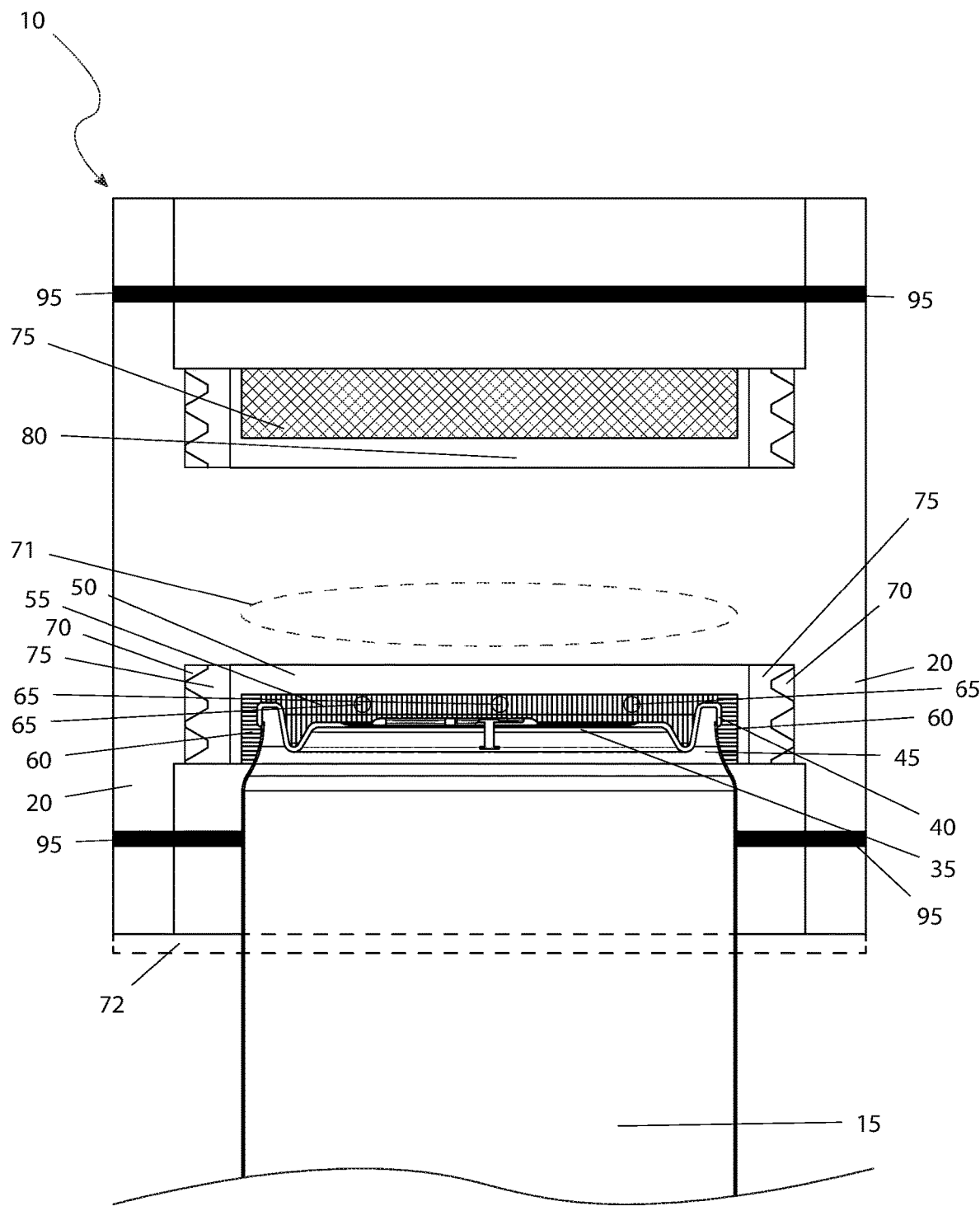
FIG. 2 is a sectional view of the beverage container sanitizing device 10, as seen along a Line I-I, as shown in FIG. 1, in use with a can bristle insert 50, according to the preferred embodiment of the present invention.

Referring next to FIG. 2, a sectional view of the device 10, as seen along a Line I-I, as shown in FIG. 1, in use, further having a first end with a can bristle insert 50 and, on the opposing second end, a can wiping pad insert 75, according to the preferred embodiment of the present invention is depicted. The can bristle insert 50 provides for both vertical bristles 55 and horizontal bristles 60 that contact the can top 35, the can rim 40, and the can sides 45. Several drops of a non-toxic food-safe liquid sanitizer 65 are added to the vertical bristles 55 and the horizontal bristles 60 to facilitate the cleaning process. The can bristle insert 50 is held within the first outer housing 20 by the use of a first threaded connection 70. The first threaded connection 70 allows for removal of the can bristle insert 50 for purposes of cleaning, replacement of usage of the first outer housing 20 with other inserts as will be described in greater detail below. A sanitizer reservoir 71 is located in the upper portion of the first outer housing 20 to hold a food safe sanitizing liquid, such as "Purely Foodservice Surface Sanitizer" or equal. A collapsible section 95 is provided on the first outer housing 20 to provide for compact storage of the device 10 when not in use.

Located on the second end of the device 10 is the can wiping pad insert 75. This view further discloses the first threaded connection 70 between the first outer housing 20 and the can wiping pad insert 75. The absorbent pad 80 is located immediately on the interior of the can wiping pad insert 75 with the center field of the can wiping pad insert 75 being completely covered with the absorbent pad 80. A protective cover 72, herein shown by dashed lines to indicate its respective place when the beverage can 15 is removed, is shown on the bottom of the first outer housing 20 to protect the interior of the device 10, from contamination when not in use.

Figure 3:
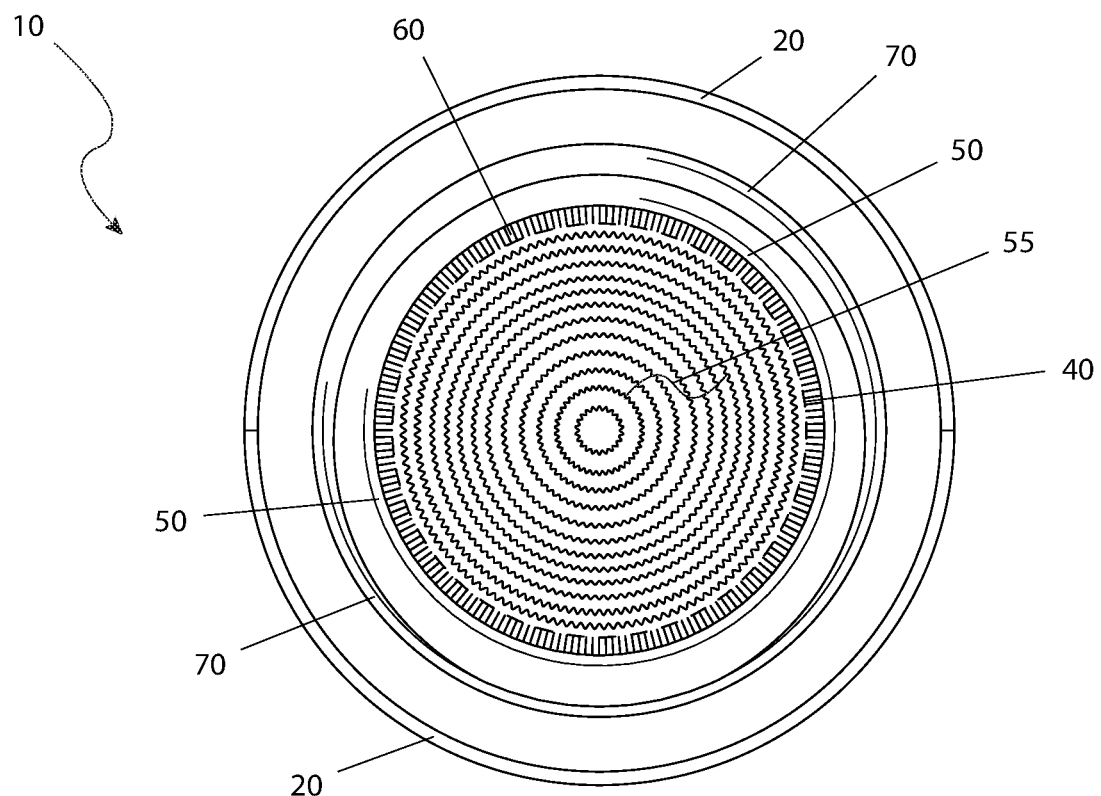
FIG. 3 is a sectional view of the beverage container sanitizing device 10, as seen along a Line II-II, as shown in FIG. 1, in use with a can bristle insert 50, according to the preferred embodiment of the present invention.

Referring now to FIG. 3, a sectional view of the device 10, as seen along a Line II-II, as shown in FIG. 1, in use with a can bristle insert 50, according to the preferred embodiment of the present invention is shown. This view further discloses the first threaded connection 70 between the first outer housing 20 and the can bristle insert 50. The horizontal bristles 60 are located immediately on the interior of the can bristle insert 50 with the center field of the can bristle insert 50 being completely covered with the vertical bristles 55. The can rim 40 is depicted by dashed lines for purposes of clarity.

Figure 4:
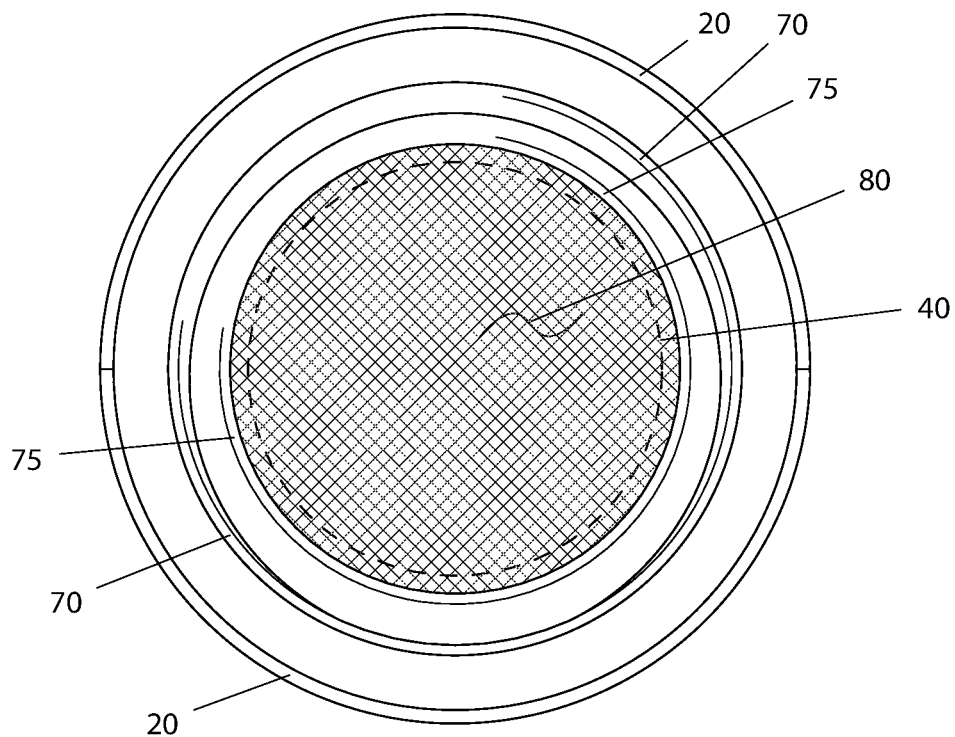
FIG. 4 is a sectional view of the beverage container sanitizing device 10, as seen along a Line I-I, as shown in FIG. 1, in use with a can wiping pad insert 75, according to the preferred embodiment of the present invention.

Referring next to FIG. 4, a sectional view of the device 10, as seen along a Line I-I, as shown in FIG. 1, in use with a can wiping pad insert 75, according to the preferred embodiment of the present invention is disclosed. The can wiping pad insert 75 provides for an absorbent pad 80 that contacts the can top 35, the can rim 40, and the can sides 45. The absorbent pad 80 removes the remnants of the food-safe liquid sanitizer 65 (as shown in FIG. 2). The can wiping pad insert 75 is held within the first outer housing 20 by the use of the first threaded connection 70. The first threaded connection 70 allow for removal of the can wiping pad insert 75 for purposes of cleaning, replacement, or usage of the first outer housing 20 with the can bristle insert 50 (as shown in FIG. 2). A collapsible section 95 is shown on the first outer housing 20 to provide for compact storage of the device 99 when not in use. As aforementioned described, the protective cover 72, herein shown by dashed lines to indicate its respective place when the beverage can 15 is removed, is shown on the bottom of the outer housing 20 to protect the interior of the device 99, from contamination when not in use.

Figure 5:
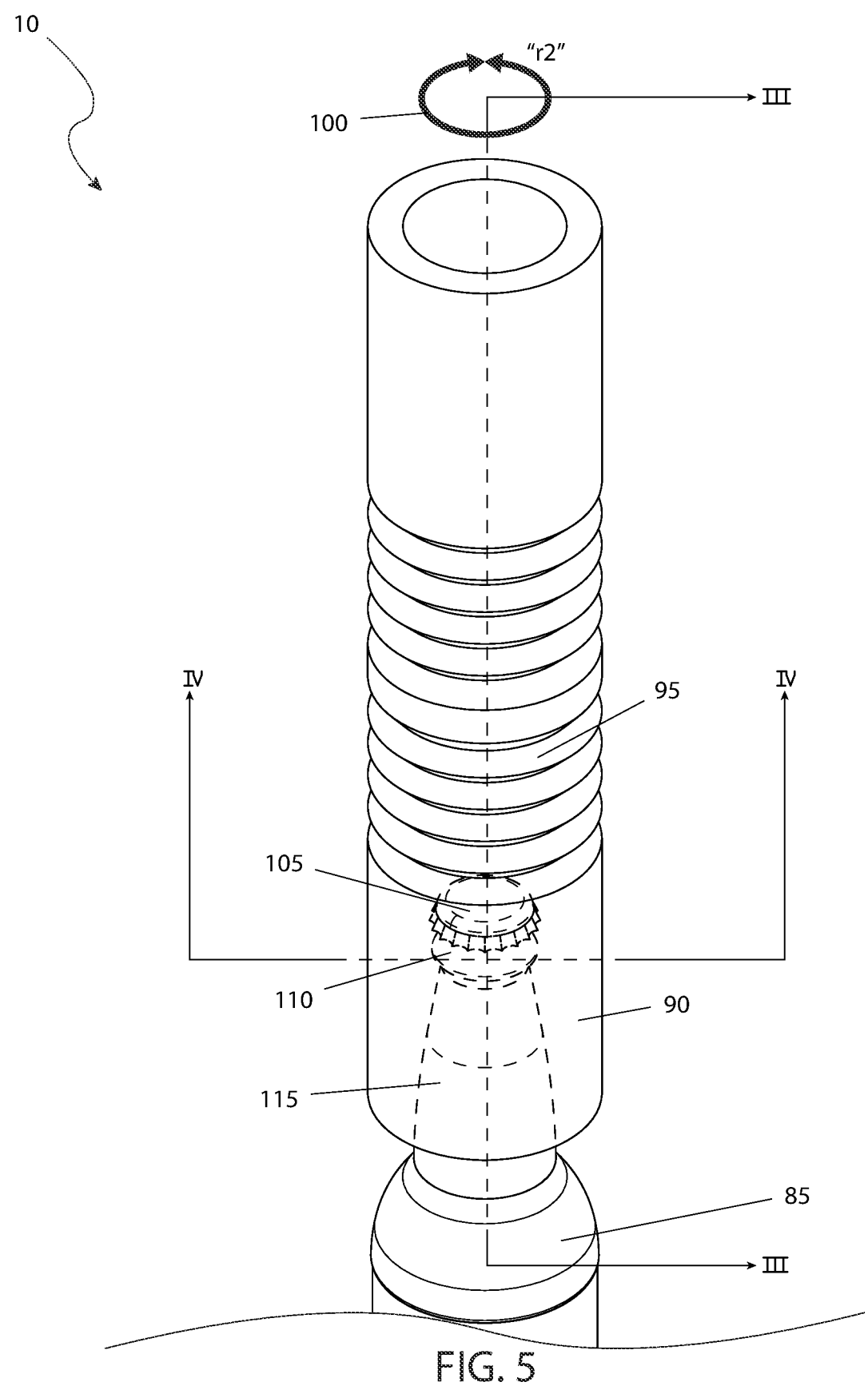
FIG. 5 is a perspective view of the beverage container sanitizing device 10, according to an alternate embodiment of the present invention.

Referring next to FIG. 5, a perspective view of the device 10, according to the alternate embodiment of the present invention is shown. The alternate embodiment is designed to clean the top of a beverage bottle 85. It includes a second outer housing 90 that sits atop the beverage bottle 85 it is approximately three inches (3 in.) tall. The second outer housing 90 is provided with a collapsible section 95 that allows the second outer housing 90 to be reduced in size to approximately two inches (2 in.) tall to save on space storage requirements when not being used. The second outer housing 90 is turned back and forth along a second rotating travel path "r2" 100, in relation to the beverage bottle 85 during the cleaning process. The cleaning process, to be further described herein below, provides for the cleaning of the bottle top 105, the bottle cap 110, and the upper portion of the bottle sides 115 and is performed before the beverage bottle 85 is opened.

Figure 6:
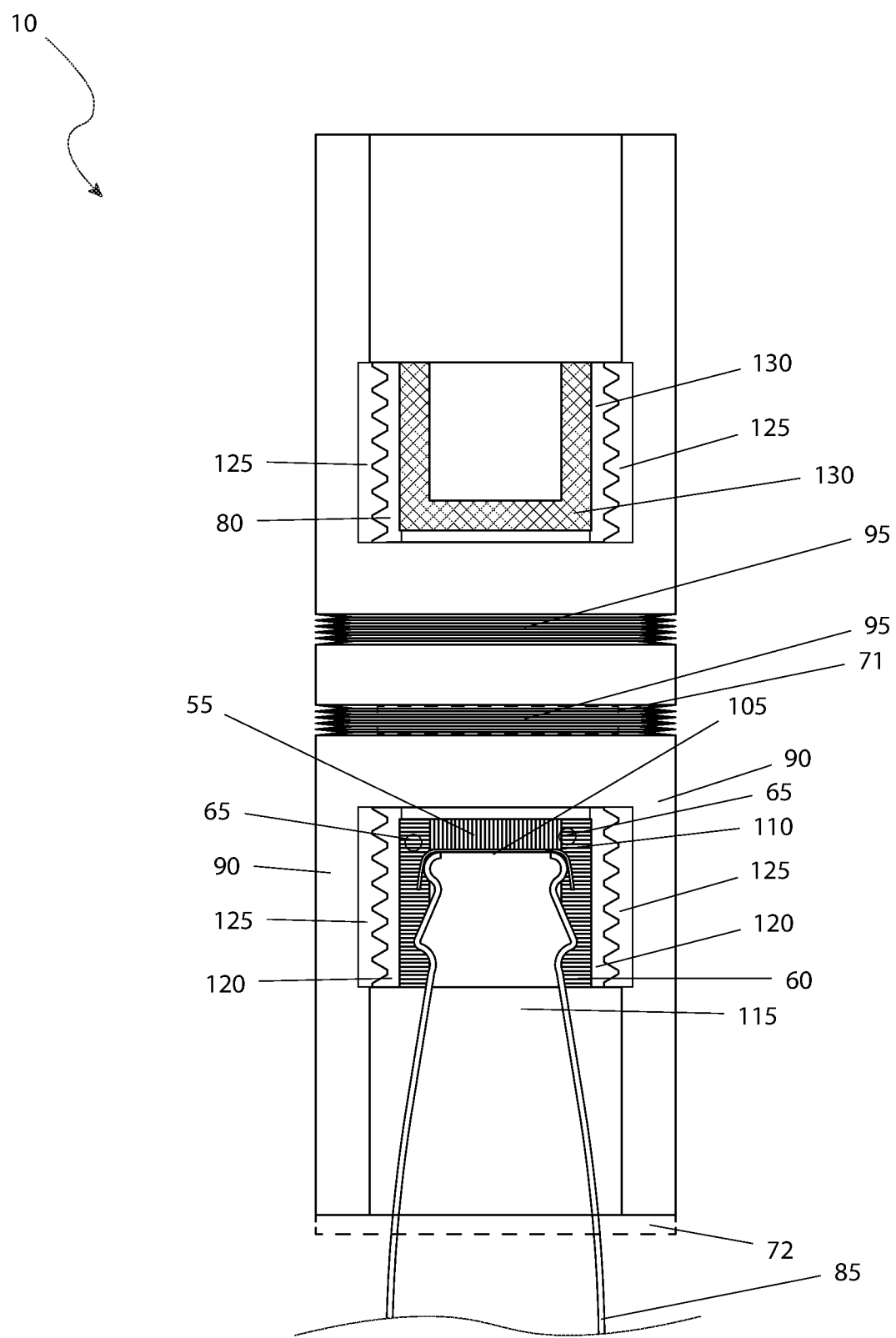
FIG. 6 is a sectional view of the beverage container sanitizing device 10, as seen along a Line III-III, as shown in FIG. 5, in use with a bottle bristle insert 120, according to the alternate embodiment of the present invention.

Referring now to FIG. 6, a sectional view of the device 10, as seen along a Line III-III, as shown in FIG. 5, in use, further having a first end with a bottle bristle insert 120 and, on the opposing second end, a can wiping pad insert 75. The bottle bristle insert 120 provides for both vertical bristles 55 and horizontal bristles 60 that contact the bottle top 105, the bottle cap 110, and the bottle sides 115. Several drops of a non-toxic food-safe liquid sanitizer 65 are added to the vertical bristles 55 and the horizontal bristles 60 to facilitate the cleaning process. The bottle bristle insert 120 is held within the beverage bottle 85 by the use of a second threaded connection 125. The second threaded connection 125 allows for removal of the bottle bristle insert 120 for purposes of cleaning, replacement, or usage of the second outer housing 90 with other inserts as will be described in greater detail below. A sanitizer reservoir 71 is located in the upper portion of the first outer housing 20 to hold a food safe sanitizing liquid, such as "Purely Foodservice Surface Sanitizer" or equal. A collapsible section 95 is provided on the first outer housing 20 to provide for compact storage of the device 10 when not in use.

Located on the second end of the device 10 is the bottle wiping pad insert 130. This view further discloses the second threaded connection 125 between the second outer housing 90 and the bottle wiping pad insert 130. The absorbent pad 80 is located immediately on the interior of the bottle wiping pad insert 130 with the center field of the bottle wiping pad insert 130 being completely covered with the absorbent pad 80. A protective cover 72, herein shown by dashed lines to indicate its respective place when the beverage bottle 85 is removed, is shown on the bottom of the second outer housing 90 to protect the interior of the device 10, from contamination when not in use.

Figure 7:
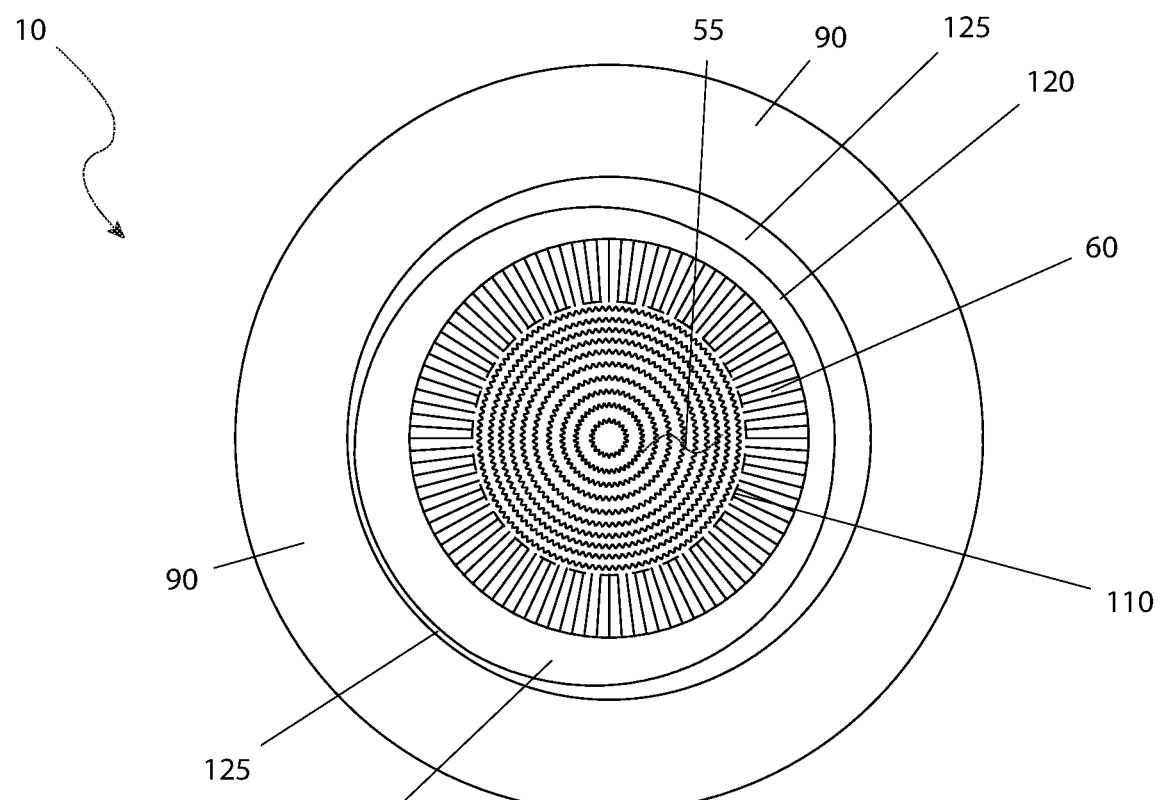
FIG. 7 is a sectional view of the beverage container sanitizing device 10, as seen along a Line IV-IV, as shown in FIG. 5, in use with a bottle bristle insert 120, according to the alternate embodiment of the present invention; and, FIG. 8 is a sectional view of the beverage container sanitizing device 10, as seen along a Line III-III, as shown in FIG. 5, in use with a bottle wiping pad insert 130, according to the alternate embodiment of the present invention.

Referring next to FIG. 7, a sectional view of the device 10, as seen along a Line IV-IV, as shown in FIG. 5, in use with a bottle bristle insert 120, according to the alternate embodiment of the present invention is depicted. This view further discloses the second threaded connection 125 between the second outer housing 90 and the bottle bristle insert 120. The horizontal bristles 60 are located immediately on the interior of the bottle bristle insert 120 with the center field of the bottle bristle insert 120 being completely covered with the vertical bristles 55. The bottle cap 110 is depicted by dashed lines for purposes of clarity.

Figure 8:
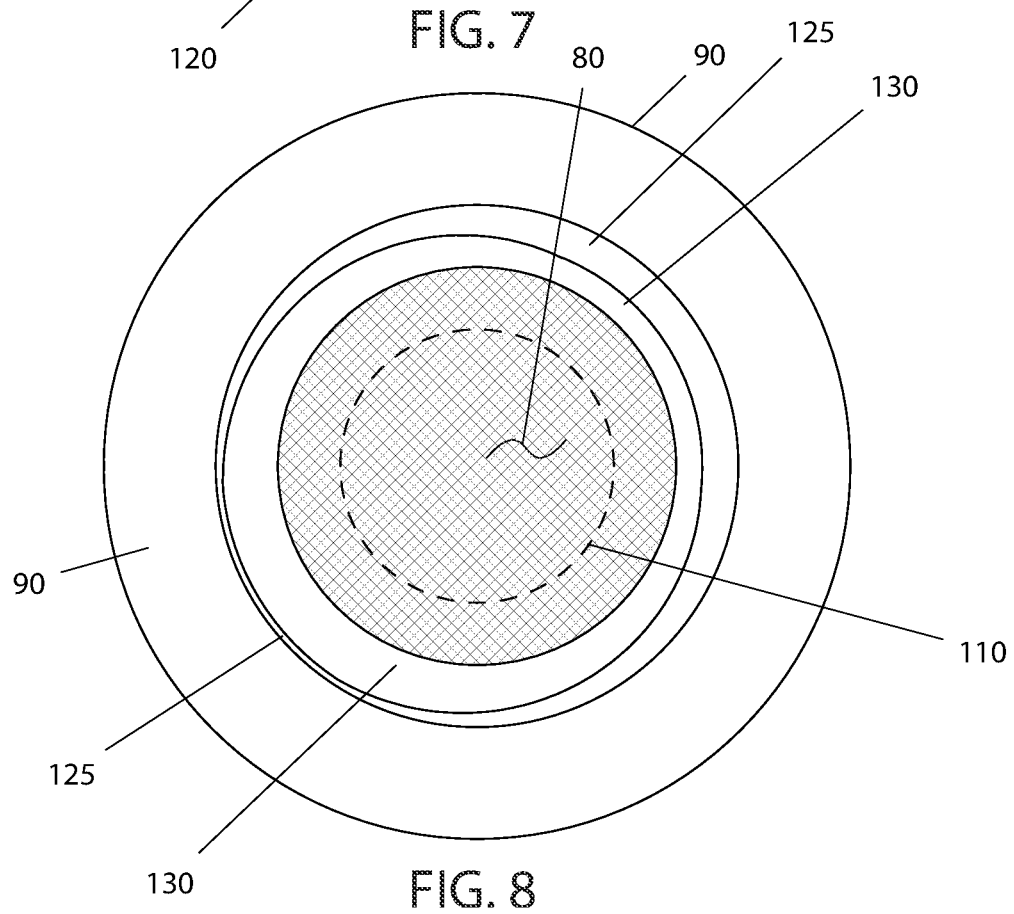

Referring now to FIG. 8, a sectional view of the device 10, as seen along a Line III-III, as shown in FIG. 5, in use with a bottle wiping pad insert 130, according to the alternate embodiment of the present invention is shown. The bottle wiping pad insert 130 provides for an absorbent pad 80 that contacts the bottle top 105, the bottle cap 110, and the bottle sides 115. The absorbent pad 80 removes the remnants of the food-safe liquid sanitizer 65 (as shown in FIG. 6). The bottle wiping pad insert 130 is held within the second outer housing 90 by the use of the second threaded connection 125. The second threaded connection 125 allow for removal of the bottle wiping pad insert 130 for purposes of cleaning, replacement, or usage of the second outer housing 90 with the bottle bristle insert 120 (as shown in FIG. 6). As aforementioned described, the protective cover 72, herein shown by dashed lines to indicate its respective place when the beverage bottle 85 is removed, is shown on the bottom of the second outer housing 90 to protect the interior of the device 10, from contamination when not in use.

2. Operation of the Preferred Embodiment

The preferred embodiment of the present invention can be utilized by the common user in a simple and effortless manner with little or no training. It is envisioned that the device 10 would be constructed in general accordance with FIG. 1 through FIG. 10. The user would procure the device 10 from conventional procurement channels such as convenience stores, discount stores, department stores, mail order and internet supply houses and the like. Special attention would be paid to the need for the preferred embodiment of FIG. 1 or the alternate embodiment of FIG. 6.

After procurement and prior to utilization, the device 10 would be prepared in the following manner: the user would select the preferred side of the first outer housing 20 of the preferred embodiment or the preferred side of the second outer housing 90 of the alternate embodiment for a beverage can 15 or a beverage bottle 85, respectively. If the first side of the preferred embodiment is selected, the can bristle insert 50 would be inserted into the first outer housing 20, or if the first side of the alternated embodiment is selected, the bottle bristle insert 120 would be inserted into the second outer housing 90; and food-safe liquid sanitizer 65 would be added to the sanitizer reservoir 71. At this point in time, the beverage container sanitizing device 10 is ready for use.

During utilization of the device 10, the following procedure would be initiated: in the case of use of the first side of the preferred embodiment of the device 10 with a beverage can 15, the first outer housing 20 is placed over the top of the beverage can 15 such that the vertical bristles 55 and the horizontal bristles 60 are in contact with the can top 35, the can rim 40, and the can sides 45; the first outer housing 20 is then moved along the first rotating travel path "r1" 25 for a suitable period of time; the first outer housing 20 is removed from the beverage can 15; and, the can bristle insert 50 may then be removed via the first threaded connection 70. In the case of use of the second side of the preferred embodiment of the device 10, the can wiping pad insert 75 is verified to be installed; the first outer housing 20 is the placed back atop the beverage can 15 and the rotational action along the first rotating travel path "r1" 25 is repeated. Once finished, the first outer housing 20 is then removed and the beverage can 15 is safe to open and drink from.

In the case of use of the first side of the alternate embodiment of the device 10 with a beverage bottle 85, the second outer housing 90 is placed over the top of the beverage bottle 85 such that the vertical bristles 55 and the horizontal bristles 60 are in contact with the bottle top 105, the bottle cap 110, and the bottle sides 115; the second outer housing 90 is then moved along the second rotating travel path "r2" 100 for a suitable period of time; the second outer housing 90 is removed; and the bottle bristle insert 120 may then be removed via the second threaded connection 125. In the case of use of the second side of the alternate embodiment of the device 10, the bottle wiping pad insert 130 is verified to be installed; the second outer housing 90 is the placed back atop the beverage bottle 85 and the rotational action along the second rotating travel path "r2" 100 is repeated. Once finished, the second outer housing 90 is then removed and the beverage bottle 85 is safe to open and drink from.

After use of the device 10, the can bristle insert 50, the can wiping pad insert 75, the bottle bristle insert 120, and the bottle wiping pad insert 130 are removed from either the first outer housing 20 or the second outer housing 90 and cleaned, rinsed and allowed to dry, thus preparing the device 10 for future and repeating use.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A beverage container sanitizing device consisting of:
    a first outer housing adapted to be disposed on top of a beverage can, comprising:
        a collapsible section for compact storage;
        a plurality of anti-slip protrusions on the first outer housing top to facilitate a turning process during cleaning;
        wherein the first outer housing is adaptable in height;
        a sanitizer reservoir located on an upper portion for holding a sanitizing liquid;
        a protective cover located on a bottom of the outer housing to protect the device's interior from contamination when not in use;
        a can bristle insert at a first end of the first outer housing, comprising:
            a plurality of vertical and horizontal bristles, adapted to contact a can top, a can rim, and a plurality of can sides; the bristles infused with several drops of a non-toxic food-safe liquid sanitizer to facilitate cleaning;
            a first threaded connection allowing for removal of the can bristle insert for cleaning, replacement, or usage of the first outer housing with other inserts;
        a can wiping pad insert at a second end of the first outer housing, comprising:
            an absorbent pad designed to contact the can top, rim, and sides to remove remnants of the sanitizer; and,
    wherein the first threaded connection enabling removal of the can wiping pad insert for cleaning, replacement, or usage; and,
    wherein the first outer housing is capable of being turned back and forth along a first rotating travel path "r1" in relation to the beverage can.

* * * * *